US00PP23314P2

(12) United States Plant Patent
Kordes

(10) Patent No.: US PP23,314 P2
(45) Date of Patent: Jan. 8, 2013

(54) FLORIBUNDA ROSE PLANT NAMED 'KORFLOCI52'

(50) Latin Name: *Rosa hybrida*
Varietal Denomination: KORfloci52

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/200,268

(22) Filed: Sep. 21, 2011

(51) Int. Cl.
*A01H 5/00* (2006.01)

(52) U.S. Cl. ..... Plt./145

(58) Field of Classification Search ..... Plt./145
See application file for complete search history.

*Primary Examiner* — Annette Para

(57) ABSTRACT

A new and distinct variety of rose with long lasting, novel yellow flowers, and attractive foliage with good disease resistance. It exhibits compact, bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci52'.

The new variety of rose plant of the present invention originated from a controlled crossing in a breeding program of two distinct parents during the summer of 2003. The crossing was between an 'un-named seedling', and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci52'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower size of 'KORfloci52' is medium while the flower size of the seed parent is very large.
2. The petal count of "KORfloci52' is semi-double while the petal count of the seed parent is very double.

The new rose plant may be distinguished from its pollen parent, an 'un-named seedling' by the following combination of characteristics:

1. The foliage of "KORfloci52' is very glossy while the foliage of the pollen parent is matte.
2. The growth habit of 'KORfloci52' is bushy and upright while the growth habit of the pollen parent is spreading.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfloci52' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci52' was selected in May, 2004 from the seedling beds to be asexually propagated for further evaluation. The first asexual propagation of 'KORfloci52' was done by budding to seedling understocks in July, 2004 at the inventor's nursery in Offenseth-Sparrieshoop, Germany.

This initial and other subsequent propagations conducted in controlled environments demonstrate that 'KORfloci52' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci52'.

DETAILED BOTANICAL DESCRIPTION

The following is a description of 'KORfloci52', as observed growing in June, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORfloci01', a rose variety from the same inventor described and illustrated in U.S. Plant Pat. No. 21,198 and issued on Aug. 17, 2010 are compared to 'KORfloci52' in Chart 1.

CHART 1

| Characteristic | 'KORfloci52' | 'KORfloci01' |
|---|---|---|
| Flower color, General tonality: | Yellow Group 7B. | Orange group 27C. |
| Flower fragrance: | None. | Light. |
| Receptacle size: | 10 mm (h) × 8 mm (w). | 5-6 mm (h) × 7-8 mm (w). |

Parents:

*Seed parent*.—An 'un-named seedling'.

*Pollen parent*.—An 'un-named seedling'.

Classification:

*Botanical classification*.—*Rosa hybrida* 'KORfloci52'.

*Commercial classification*.—Floribunda rose.

FLOWER AND FLOWER BUD

Blooming habit: Continuous.

Flower bud:

*Size*.—Upon opening, 25 mm in length from base of receptacle to distal end of bud and 20 mm diameter at its widest point.

*Bud form*.—Short. Pointed ovoid.

*Bud color*.—As sepals first unfold, bud color is Yellow Group 11A. When ¼ open, the upper surface of petals is Yellow Group 12A, and the lower surface is Yellow Group 13C.

*Sepals*.—Color: Upper surface Green Group 138B. Lower surface Green Group 138C with intonations of Greyed-Purple Group 185B and 185C on upper and lower surfaces. Size: Average 25-30 mm (l)×8-10 mm (w). Shape: Triangular. Strong foliaceous appendages on three of the five sepals. Apex: Apiculate. Base: Flat at union with receptacle. Quantity: Five. Surface texture: Upper side: Strongly pubescent. Lower surface: Lightly pubescent. Margins: Pubescent with stipitate glands.

Receptacle:

*Surface*.—Smooth.

*Color*.—Yellow-Green Group 144A.

*Shape*.—Pear shaped.

*Size*.—10 mm (h)×8 mm (w).

Peduncle:

*Surface*.—With very few fine hairs and stipitate glands.

*Length*.—30 to 45 mm average length.

*Diameter*.—2 to 4 mm average diameter.

*Color*.—Yellow-Green Group 146C.

*Strength*.—Somewhat strong.

*Borne*.—Multiple flower buds per stem, generally 2 to 5.

Flower bloom:

*Fragrance*.—None.

*Duration*.—On the plant 5-7 days. As a cut flower, 3 to 5 days. Senesced petals drop away cleanly.

*Size*.—Medium sized for a floribunda rose. When open, the average flower diameter is 80 mm and the average flower height is 25-35 mm.

*Form*.—Shape of flower when viewed from the side: Upon opening, upper part: Flat. Upon opening, lower part: Concave. Open flower, upper part: Flat. Open flower, lower part: Concave.

Color:

*Upon opening, petals*.—Outermost petals: Outer Side: Yellow Group 13C. Inner Side: Yellow Group 12A. Innermost petals: Outer Side: Yellow Group 13C. Inner Side: Yellow Group 13B.

*Upon opening, basal petal spots*.—No distinctive coloration at petal base observed.

*After opening, petals*.—Outermost petals: Outer Side: Yellow Group 7B. Inner Side: Yellow Group 8A. Innermost petals: Outer Side: Yellow Group 11B. Inner Side: Yellow Group 11A.

*After opening, basal petal spots*.—Basal petal spot, outermost petals: Outer Side: Yellow Group 13B. Inner Side: Yellow Group 13B. Basal petal spot, innermost petals: Outer Side: Yellow Group 11A. Inner Side: Yellow-Orange Group 14B.

General tonality: On open flower Yellow Group 7B. No change in the general tonality at the end of the 4th day. Afterwards, general tonality is Yellow Group 10B and 10C.

Petals:

*Petal count*.—Double. Average Range: Approximately 25-30 petals under normal conditions.

*Petal reflex*.—Petals reflex slightly.

*Petal edge*.—Entire.

*Petal shape*.—Ovate. Apex shape is ovate. Shape of base is acute.

*Petal size*.—40 mm (l)×35 mm (w).

*Thickness*.—Thin.

*Petal arrangement*.—Not Formal.

Petaloid count: Average of 1-4 per flower.

*Petaloid size*.—Petaloids are 10-15 mm (l) and 5 mm (w).

*Petaloid color*.—Color of inner side is Yellow Group 10C. Color of outer side is Yellow Group 10C.

*Petaloid texture*.—Fine.

*Margins*.—Undulated.

*Petaloid shape*.—Overall: Deltoid. Apex: Ovate. Base: Acute.

Reproductive organs:

*Pistils*.—Average. Approximately 25 present. Stigmas: Location: Slightly inferior in position to anthers. Color: Yellow Group 13A at apex with distal portion Red Group 53C and 53D. Styles: Length: About 7 mm long. Color: Yellow-Green Group 145A.

*Stamens*.—Approximately 50 on average and regularly arranged around the styles. Anthers: Size: Average 1 mm long. Pollen: Generally present. Color: Greyed-Orange Group 167A. Filaments: Color: Yellow-Orange Group 15B. Length: About 6-8 mm long.

THE PLANT

Growth: Moderate growth.

Plant habit: Compact bushy habit. When grown as a budded field plant, the average plant height is 70 cm and the average plant width is 60 cm.

Stems:

*Stem color*.—Juvenile stems: Yellow-Green Group 146C. Mature stems: Yellow-Green Group 146A.

*Stem surface*.—Juvenile stems: Smooth. Mature stems: Rough.

Prickles: Present.

*Incidence*.—Average of 10 per each 10 cm of stem.

*Size*.—Average length: Variable. Ranging from 2-10 mm in length on mature wood.

*Color*.—Immature prickles: Greyed-Purple Group 194A. Mature prickles: Greyed-Green Group 194C. Senescing to Greyed-Purple Group 182D.

*Shape*.—Linear to slightly concave.

*Anthocyanin*.—Present. Greyed-Purple Group 182B to 182D on immature prickles.

Leaves and leaflets: Normally 5 leaflets on normal leaves in middle of the stem.

*Venation pattern*.—Pyramidal net pattern.

*Leaf size*.—160 mm (l)×130 mm (w).

*Abundance*.—Average.

*Texture*.—Thick. Upper side of leaflet: Semi-glossy and smooth. Under side of leaflet: Matte and smooth.

Color, mature foliage:

*Upper leaf surface*.—Green Group 137B.

*Lower leaf surface*.—Green Group 137C.

Color, juvenile foliage:

*Upper leaf surface*.—Green Group 137A.

*Lower leaf surface*.—Green Group 137B.

Anthocyanin intonation: Present. Intonations of Greyed-Purple Group 183B present on juvenile leaflets.

Stipules:

*Size*.—22 mm long, 3 mm from distal tip to distal tip.

*Stipule color*.—Yellow-Green Group 146C.

*Anthocyanin*.—Greyed-Red Group 182D on upper surface.

*Stipitate glands*.—Abundant along margins.

*Shape*.—Apex: Apiculate. Base: Slightly winged.

Petiole:

*Length*.—Average 15-25 mm.

*Diameter*.—Average 2-3 mm.

*Petiole color*.—Yellow-Green Group 144A.

*Underneath*.—Numerous small prickles, occasional stipitate glands.

*Margins*.—With stipitate glands.

Petiole rachis:

*Length*.—Average 20-25 mm.

*Diameter*.—Average 2-3 mm.

*Color*.—Yellow-Green Group 146C.

*Underneath*.—Smooth with occasional prickles.

*Margins*.—With stipitate glands.

Leaflets:

*Size*.—Average size of the terminal leaflet is 70-75 mm (l)×50-60 mm (w).

*Shape*.—Base: Obtuse. Apex: Ovate.

*Margins*.—Finely serrated.

*Surface*.—Upper side: Glossy. Lower side: Matte.

*Texture*.—Thick.

*Arrangement*.—Odd pinnate.

*Venation*.—Reticulate.

Hips/seed formation: None observed.

Winter hardiness: To date, the variety has been grown successfully in Zones 5-9.

Disease resistance: Good resistance to Powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

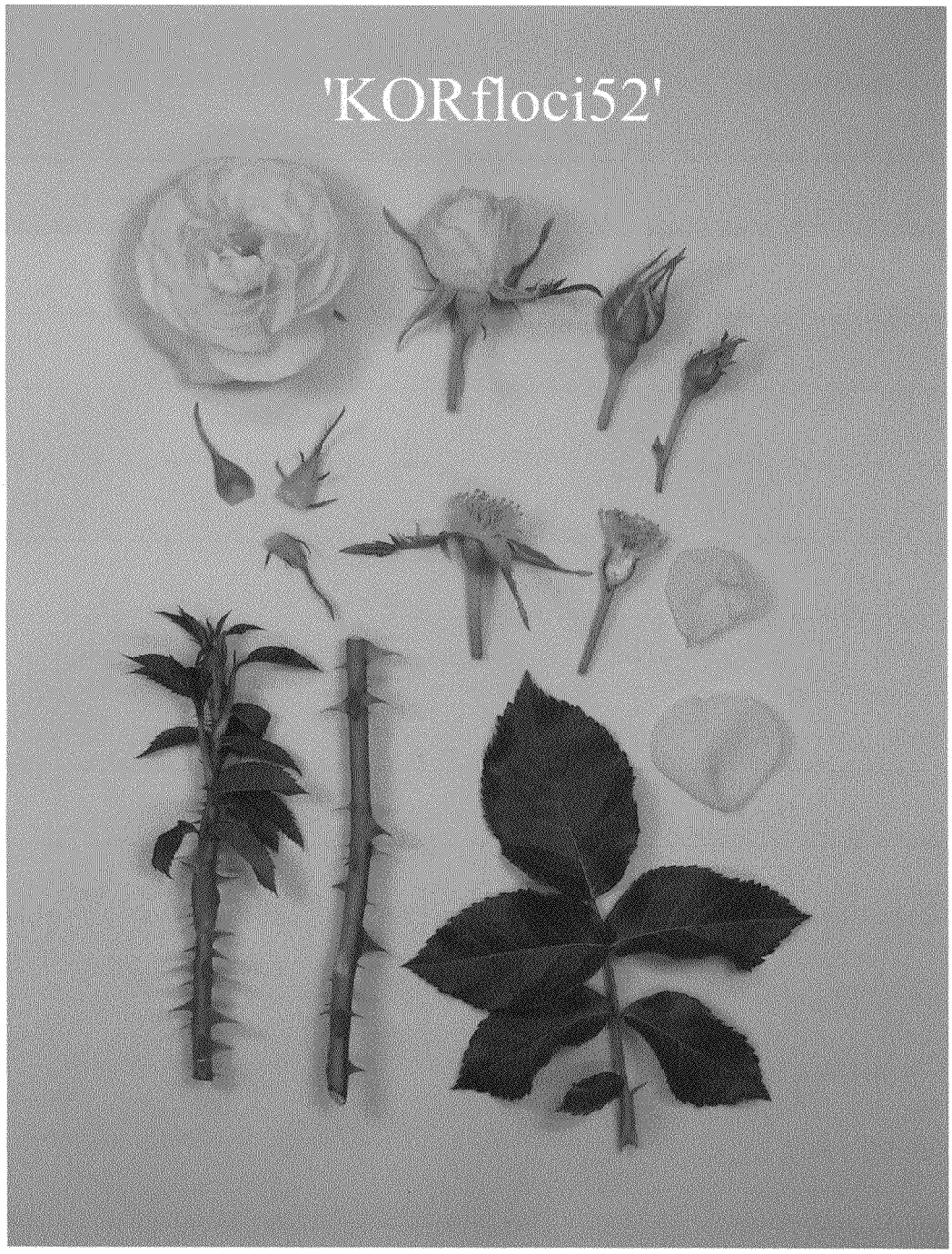
'KORfloci52'